United States Patent
Trompen et al.

(10) Patent No.: US 6,974,587 B2
(45) Date of Patent: Dec. 13, 2005

(54) INTRARUMINAL DEVICE

(75) Inventors: Mick Trompen, Westfield, IN (US); Ronald W. Lyon, Carmel, IN (US); Gregory A. Lyon, Indianapolis, IN (US)

(73) Assignee: Aircom Manufacturing, Inc., Indianapolis, IN (US)

( * ) Notice: Subject to any disclaimer, the term of this patent is extended or adjusted under 35 U.S.C. 154(b) by 513 days.

(21) Appl. No.: 10/141,300

(22) Filed: May 8, 2002

(65) Prior Publication Data

US 2003/0212386 A1 Nov. 13, 2003

(51) Int. Cl.⁷ ............................ A23K 1/18; A61F 13/00
(52) U.S. Cl. ....................................... 424/438; 424/422
(58) Field of Search ...................... 604/890.1, 891.1, 604/892.1, 131, 132, 133, 140–143; 424/438, 422

(56) References Cited

U.S. PATENT DOCUMENTS

| | | | |
|---|---|---|---|
| 3,797,492 A | 3/1974 | Place | |
| 4,265,241 A | * 5/1981 | Portner et al. | 604/131 |
| D271,623 S | 11/1983 | Simpson et al. | |
| 4,468,220 A | * 8/1984 | Willbanks | 604/140 |
| 4,874,388 A | 10/1989 | Wong et al. | |
| 4,883,484 A | * 11/1989 | Shepherd et al. | 604/891.1 |
| 5,034,229 A | 7/1991 | Magruder et al. | |
| 5,308,348 A | 5/1994 | Balaban et al. | |
| 5,318,557 A | 6/1994 | Gross | |
| 5,456,679 A | 10/1995 | Balaban et al. | |
| 5,562,915 A | 10/1996 | Lowe et al. | |
| 5,876,377 A | * 3/1999 | Kriesel | 604/133 |
| 6,132,420 A | * 10/2000 | Dionne et al. | 604/892.1 |
| 6,180,129 B1 | 1/2001 | Magruder et al. | |
| 6,245,042 B1 | * 6/2001 | Kriesel et al. | 604/132 |
| 6,485,463 B1 | * 11/2002 | Yeh | 604/132 |

* cited by examiner

*Primary Examiner*—Sharon Kennedy
(74) *Attorney, Agent, or Firm*—Pearne & Gordon LLP

(57) ABSTRACT

An intraruminal device is provided for the time release dispensation of a medicament to a ruminant. The device has no metal parts which may damage slaughterhouse equipment or injure a human upon consumption of ground meat from a ruminant from which the device was not properly removed. The device may use a nonmetallic bladder assembly having a to supply a compressive force to the medicament matrix to keep the matrix abutted against the first end of the device. The device may also use a piston to create a fluid-tight seal allowing part of the device to be pressurized, allowing the piston to provide a compressive force to the medicament matrix. The matrix surface at the first end is exposed to ruminal juices for dissolution of the matrix and dispensation of the medicament into the rumen.

17 Claims, 3 Drawing Sheets

INTRARUMINAL DEVICE

BACKGROUND OF THE INVENTION

1. Field of the Invention

The present invention relates to an intraruminal device, and more particularly to an intraruminal device for dispensing a time release medicament to a ruminant animal.

2. Description of Related Art

Domestically raised ruminant animals (e.g. goats, sheep and cattle) are typically sold by weight; the market price of such animals is proportional to their weight when sold. Ruminants are grazing animals, and are often left in open grazing fields for the entire grazing season. It is desirable that ruminants graze continuously throughout the season to gain as much weight as possible so they will fetch a high market price.

Unfortunately, many grazing fields contain bacteria which can infect grazing animals causing them to lose weight. Such bacterial infections require treatment with an antibiotic to combat the infection and ensure animal health. Ruminants are also susceptible to other forms of illness which can adversely affect their health or weight, and which must be treated with medication. Finally, farmers often wish to administer growth promoters, such as hormones, vitamins, etc., to their herd.

Such medicaments often must be administered slowly or periodically over time. It is difficult and expensive to regularly retrieve grazing animals to administer medicaments. Therefore, devices have been developed that are inserted into the rumen of such animals to control the time release administration of a medicament. Such a device is inserted when needed, for example at the beginning of the grazing season, and remains inside the rumen until the animal is slaughtered.

Existing intraruminal devices comprise a plastic housing containing a medicament matrix. The matrix is pressed against a first end of the device by a metal compression spring. Through an opening at the first end, the medicament matrix is exposed to ruminal juices which dissolve the matrix, thereby dispensing the dispersed medicament. Such devices have been shown to be effective at time releasing medicaments into the rumen. However, the metal spring in these devices is a major disadvantage.

Ideally, intraruminal devices should be retrieved from animals prior to processing. However, given the sheer volume of animals slaughtered each year, it is impossible to ensure proper removal of a present intraruminal device from each. Consequently, some intraruminal devices invariably slip through the slaughterhouses where they are ground up and processed. Metal springs are therefore highly disadvantageous in intraruminal devices because they can damage slaughtering equipment. More importantly, the metal fragments produced pose a risk of injury to a person eating the resulting processed meat.

Other nonmetallic means of providing compressive force to expel a medicament from a medication delivery device are known; e.g., vapor pressure means as disclosed in U.S. Pat. No. 3,797,492, osmotic pressure means as disclosed in U.S. Pat. No. 5,456,679, and electrolytic means as disclosed in U.S. Pat. No. 5,318,557. However, disadvantages of these compressive means are expense and difficulty of reliably implementing them in a compact intraruminal device.

It is therefore desirable to provide an intraruminal device having a mechanically supplied compressive force to dispense a medicament matrix without introducing significant additional complexity or cost to the device. Such a device should have no metal parts that may interfere with slaughterhouse equipment or injure a human upon ingestion in cases where the device is accidentally not removed.

SUMMARY OF THE INVENTION

An intraruminal device for the time release dispensation of a medicament, said device comprising a housing having a first end and a second end, and a bladder assembly disposed within said housing, said bladder assembly comprising either a plurality of fluid bladders connected in series via bladder passageways or a fluid bladder folded inwardly on itself at least one time. The device may have alternately have a piston that creates a fluid-tight seal against the inner surface of the housing.

DETAILED DESCRIPTION OF THE INVENTION

Figure 1:
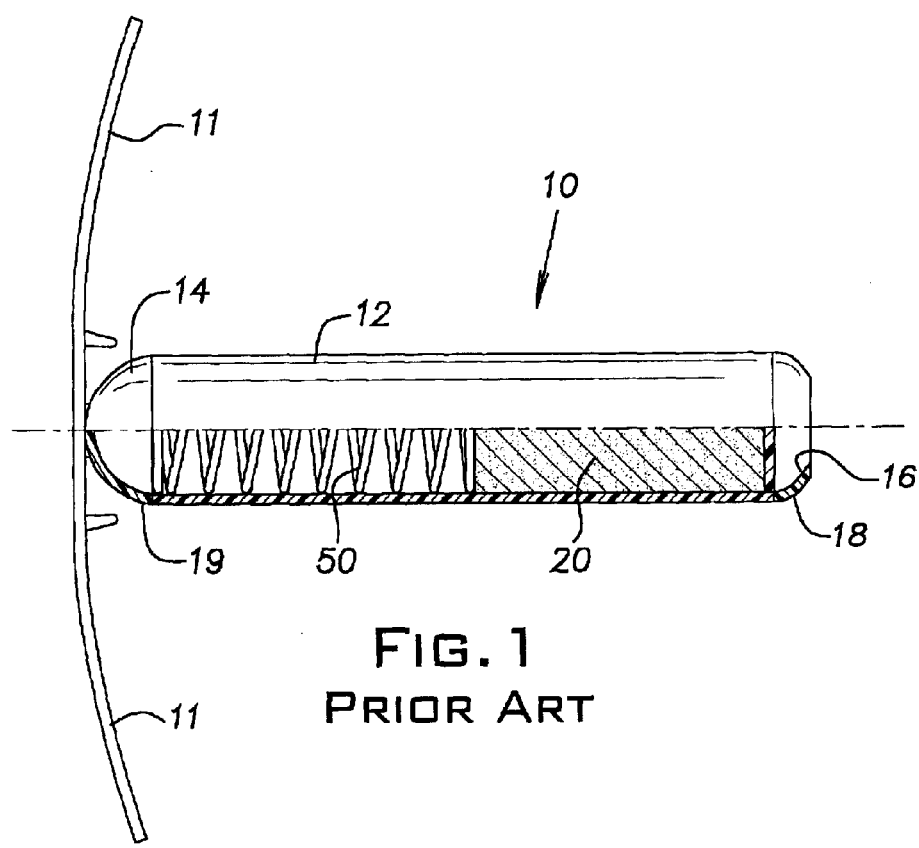
FIG. 1 is side view, partially in section, of an intraruminal device having a metal compressive spring characteristic of the prior art.

Referring first to FIG. 1, an intraruminal device having a metal compressive spring characteristic of the prior art is shown. The device 10 has a device housing 12, a cap 14, retention wings 11, and a metal compression spring 50. The retention wings 11 prevent an animal from passing or regurgitating the device 10 from the rumen, and can be formed integrally with the cap 14 as shown in FIG. 1. Alternatively, wings 11 may be formed integrally with the housing 12. Less preferably, wings 11 can be formed separately and attached via known means to the device 10. The device may also be formed without wings. Such wingless design generally are weighted to ensure that they remain in the rumen. The housing, cap and retention wings are all made of nonmetallic materials, preferably plastic, preferably polytetrafluoroethylene (PTFE), polychlorotrifluoroethylene (PCTFE), ethylene tetrafluoroethylene (ETFE), polyvinylidene fluoride (PVDF), polyvinyl chloride (PVC), ABS plastic, polyethylene, or any other plastic compatible with ruminal fluids that has a softening point above the ruminal temperature; i.e., above 42° C., preferably above 50° C. The housing 12 has a first end 18 and a second end 19. A medicament matrix 20 is disposed in housing 12 adjacent the first end 18, and is retained therein by an inwardly extending lip 16. Except for the lip 16, the first end 18 of the housing shown in FIG. 1 is typically substantially open and unobstructed. Matrix 20 is held against lip 16 by a compressive force imparted by metal spring 50. The spring is attached to the second end 19 of housing 12 at cap 14. Within an animal's rumen, the device dispenses medicament from matrix 20 over time by compressing the matrix against lip 16 so that the surface of the matrix is exposed to and dissolved by the ruminal juices. As the exposed surface of matrix 20 erodes, the metal spring 50 continues to force the matrix against lip 16, ensuring that newly exposed matrix surface remains in contact with the ruminal juices so the process may continue. Metal spring 50 thus ensures dissolution of the entire matrix and time-release of the medicament.

Figure 2:
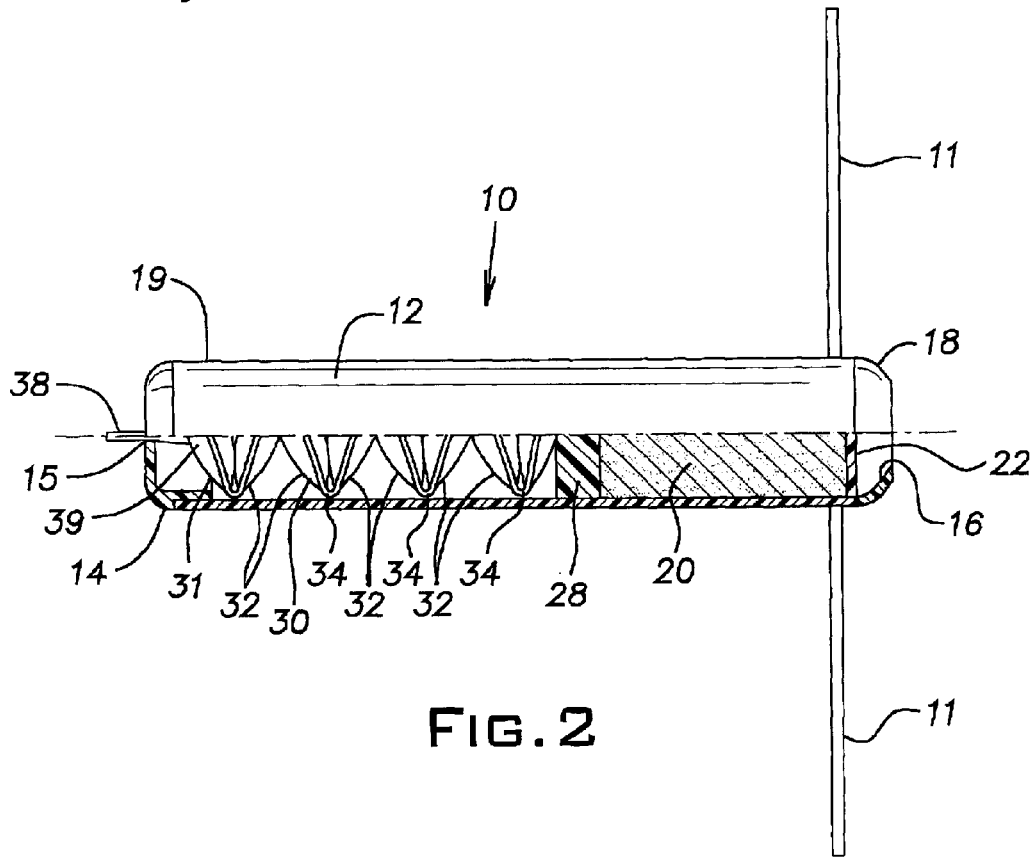
FIG. 2 is a side view, partially in section, of an intraruminal device showing a bladder assembly according to a first embodiment of the present invention.

Referring now to FIG. 2, a first embodiment of the invention is shown. The device is substantially similar to the device shown in FIG. 1 and described above, except that metal spring 50 has been replaced with bladder assembly 30. Bladder assembly 30 has a leading fluid bladder 31 and a number of subsequent fluid bladders 32 connected in series via bladder passageways 34. Passageways 34 provide fluid communication between all of the bladders 31,32 in the bladder assembly 30. Leading bladder 31 has a fluid delivery tube 38 for inflation or pressurization of the bladder assembly with a pressurizing fluid. Delivery tube 38 has a check valve 39 or other means of retaining fluid pressure therein. The check valve permits a pressurizing fluid to pass from a fluid source through tube 38 into the leading bladder 31 but not in the reverse direction from the leading bladder 31 to the outside. Check valve 39 has a cracking pressure of preferably at least 0.1, more preferably at least 0.5 psid.

Figure 3:
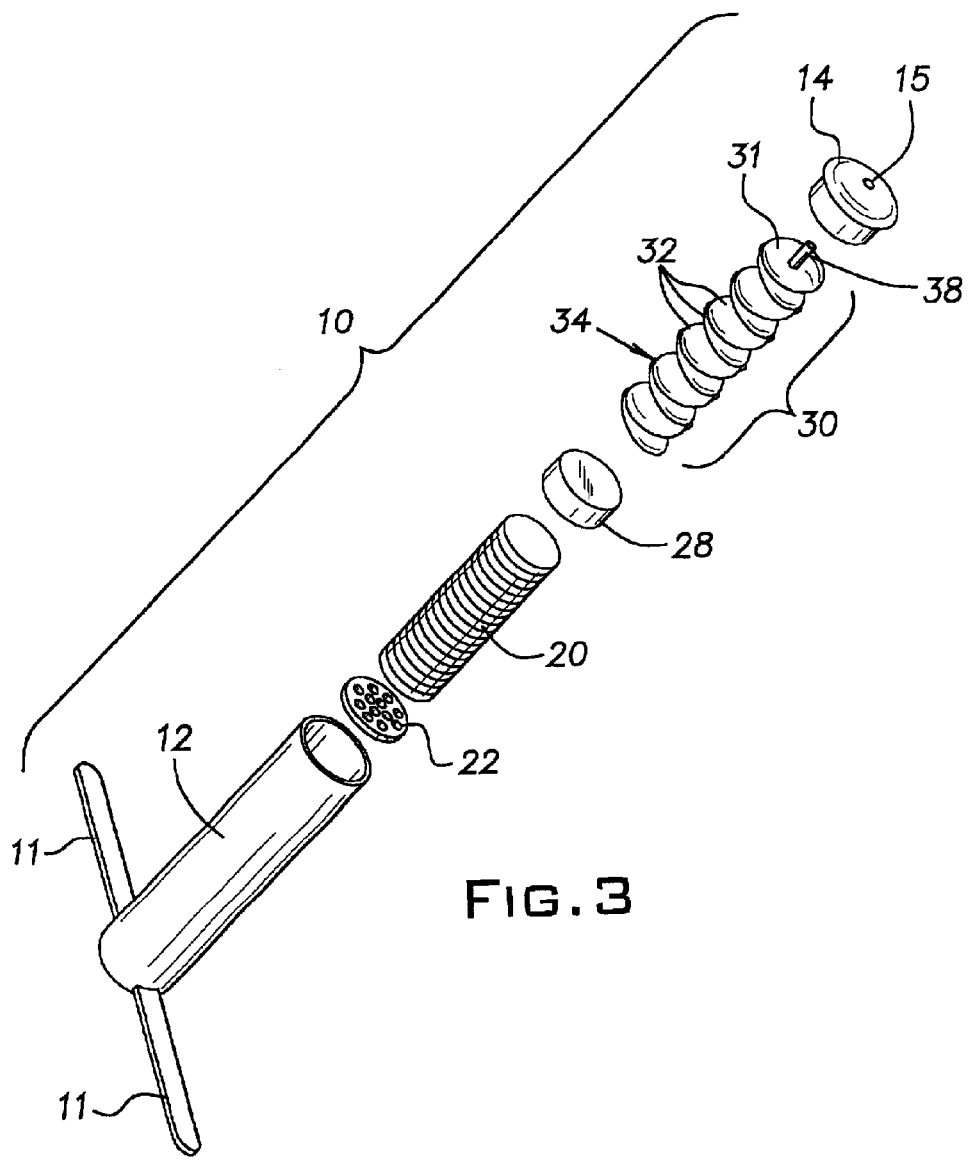
FIG. 3 is an exploded perspective centerline view of the device shown in FIG. 2.

Bladder assembly 30 preferably is made from two halves wherein each half is preformed in the shape of a bladder assembly blank. The blanks are preferably formed from a flexible elastomeric material. Bladder assembly blanks can have different shapes depending upon the desired shapes of individual bladders 31,32 in the bladder assembly 30. For example, the blank shown in FIG. 4 will yield a bladder assembly having bladders 31,32 as shown in FIGS. 2–3. Such a bladder assembly, having circular bladders, is designed to fit in a cylindrical housing 12. However, bladder assemblies having square, oval, polygonal, or otherwise shaped bladders can be fashioned to accommodate correspondingly shaped housings as will be understood by one skilled in the art.

Figure 4:
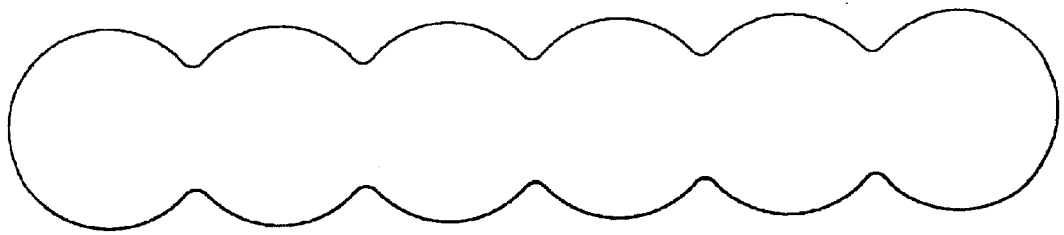
FIG. 4 is a plan view showing the shape of a preformed bladder assembly blank according to the present invention.

Returning to FIG. 4, the bladder assembly blank represents one half of a bladder assembly. Two such blanks are joined together in register with one another and sealed at the edges thereof to form fluid bladders 31,32 joined by bladder passageways 34 as previously described and shown in FIGS. 2–3. A bladder assembly having individual bladders 31,32 is preferred over a single large bladder in the first embodiment because the bladders are alternately folded one over the other in a zig-zag arrangement as shown in FIG. 4. When the bladder assembly is folded in the zig-zag arrangement, each bladder passageway will connect two bladders and will be located near the edge of the bladder, the edge of the bladder being adjacent to the housing. Each bladder except the bladders at the ends will thus have two bladder passageways leading to neighboring bladders, and the bladder passageways will be located at opposite edges of the bladder. Once inflated, the individual bladders of the zig-zag bladder assembly will expand and press against the adjacent bladders, resulting in an overall expansive tendency of the bladder assembly. The elastomeric material of the bladder assembly 30 causes the walls of individual bladders 31,32 to resist stretching that would result from compression by adjacent bladders. This stretching resistance causes the entire bladder assembly 30 to expand rather than stretch the bladder walls from such compression. Thus, the stretching resistance of bladders 31,32 cooperates with the expansive force of the pressurizing fluid to enhance the overall expansive tendency of the bladder assembly. This tendency translates into an enhanced compressive force against the matrix 20 as will be further described.

The invented intraruminal device 10 is assembled generally as shown in FIG. 3. The medicament matrix 20 and bladder assembly 30 are usually loaded into the device housing 12 through the second end 19, although they may be loaded into the device through the first end if the lip or other end with open. The bladder assembly is loaded into housing 12 in a zig-zag arrangement such that all the bladders 31,32 are substantially co-axial within housing 12 as shown in FIG. 2. Preferably, bladder assembly 30 is loaded into housing 12 in an unfilled or deflated state, meaning that pressurizing fluid has not been delivered into the bladder assembly to inflate the bladders 31,32. The cap 14 is fastened to the second end of housing 12, preferably screwed, ultrasonically welded, spin welded, glued, or compression fit, constraining the bladder assembly between the matrix 20 and the cap. Preferably, cap 14 has a hole or tube port 15 extending therethrough to accommodate fluid delivery tube 38 as best seen in FIG. 2. Optionally, a plunger or piston 28 can be inserted into the housing 12 between the bladder assembly 30 and the matrix 20.

Figures 8, 9, 10:
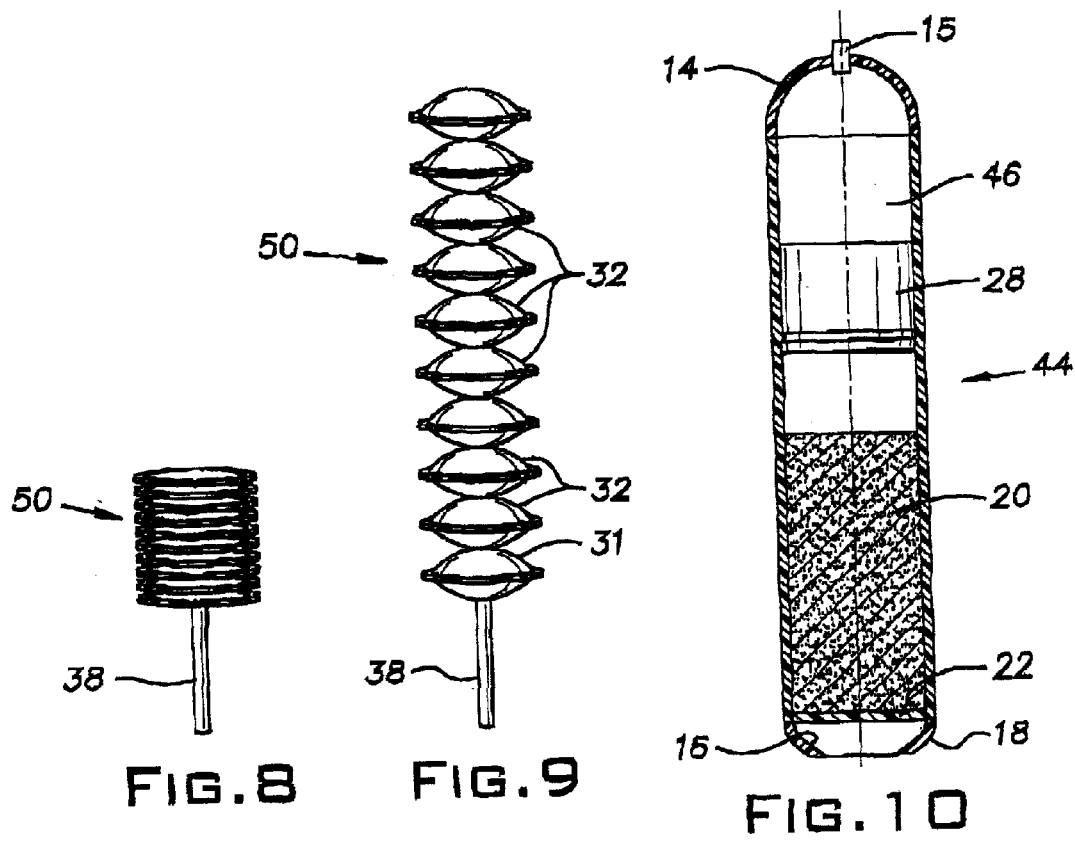
FIG. 8 is a perspective view of a bladder assembly according to a third embodiment of the invention, in a deflated condition.
FIG. 9 is a perspective view of the bladder assembly shown in FIG. 8, in an inflated condition.
FIG. 10 is an elevation view of an intraruminal device, without retention wings, in cross-section.

Alternatively, the bladder assembly may be used in an intraruminal without retention wings, as shown in FIG. 10. The bladder assembly would then be located in space 46.

Once device 10 is assembled, a pressurizing fluid source is connected to tube 38 which extends from cap 14. The pressurizing fluid is preferably a gas, most preferably air, $CO_2$, $N_2$, $O_2$, or any other gas that is harmless to ruminants, and which remains gaseous at 50, preferably 100, psi at 35° C. Bladder assembly 30 is then inflated to an initial pressure of at least 1, preferably 10, preferably 20, preferably 30, preferably 35, preferably 50 psig. Once the bladder assembly is pressurized, the intraruminal device 10 is ready for insertion into the rumen by known methods and means, such as with a balling gun.

Less preferably, the pressurizing fluid can be a liquid, such as water. Gas is preferred to liquid because liquids are substantially incompressible whereas gases are highly compressible; thus a gas-filled bladder assembly in its initial state (when matrix 20 has its initial full size) retains significant expansive potential from the expansion of the compressed gas within the bladders 31,32. By contrast, a bladder assembly filled with a substantially incompressible liquid in the initial state has little expansion potential, and will force matrix 20 firmly against lip 16 less effectively as the matrix erodes and decreases in size.

The pressurized bladder assembly 30 provides the compressive force which keeps medicament matrix 20 forced against lip 16 at the first end 18 of housing 12. Alternately, first end 18 can also have a grated wall or a flat wall with various hole patterns extending across the end of the device. Within the rumen, matrix 20 is exposed to the ruminal digestive fluids through the first end of the housing. The removal fluids dissolve or erode the matrix, resulting in dispensation of the medicament dispersed throughout the matrix. As the exposed matrix surface is dissolved or eroded, compressive force from the bladder assembly forces the newly exposed surface against lip 16 and into contact with ruminal juices.

The rate of matrix dissolution and medicament dispensation is related to the matrix composition (which controls the rate of dissolution or erosive attack by ruminal fluids), and the medicament concentration within the matrix. Compositions of medicament matrices are known in the art. A third factor related to the rate of matrix dissolution is the surface area of contact between the matrix 20 and the ruminal juices. Optionally, a porous screen or plate 22 can be inserted into the housing 12 between lip 16 and matrix 20 as shown in FIG. 2 and FIG. 3. The porous plate 22 defines holes or pores, the size of which are chosen to increase or decrease the surface area of contact between the ruminal juices and the matrix. Obviously, smaller hole or pore size results in lower contact surface area and vice versa. The hole or pore size and shape is chosen to provide the desired contact surface area that will lead to the desired dispensation rate for a particular medicament matrix. Alternatively, the first end 18 can be provided with a closed wall integrally formed with the housing 12 that has pores or holes therein.

Figures 5, 6, 7:
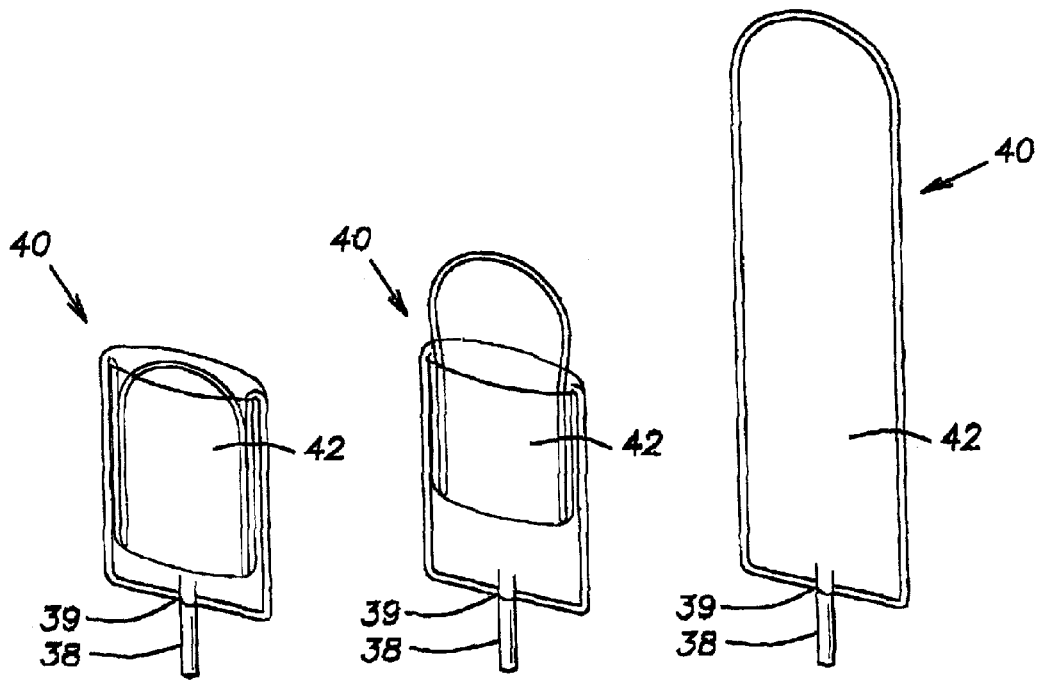
FIG. 5 is a perspective view of a bladder according to a second embodiment of the invention, in a folded configuration.
FIG. 6 is a perspective view of the bladder assembly shown in FIG. 5, shown in a partially unfolded configuration.
FIG. 7 is a perspective view of a bladder assembly shown in FIG. 5 and FIG. 6, shown in an unfolded configuration.

Referring now to FIGS. 5 through 7, a bladder assembly for use in a second embodiment of the invention is shown. The bladder assembly 40 has a fluid delivery tube 38 and check valve 39 as found in the first embodiment bladder assembly 30. The bladder assembly 40 according to the second embodiment, however, has an elongated fluid bladder 42. The fluid bladder 42 is folded inwardly upon itself. FIGS. 5 and 6 show a configuration in which the fluid bladder 42 is folded on itself twice; FIG. 5 shows the fluid bladder essentially completely folded while FIG. 6 shows the fluid bladder partially folded. FIG. 7 shows the fluid bladder completely unfolded.

While FIGS. 5 and 6 illustrate a configuration in which the fluid bladder is folded twice, the fluid bladder may be folded only once, or three or more times.

The fluid bladder 42 may be assembled from two halves using blanks of the desired shape as described in the first embodiment. The fluid bladder may have a rounded end as shown in FIGS. 5–7, or any other suitable shape, such as square. The fluid bladder may have roughly uniform width along its length. Tapering makes the fluid bladder narrower at the end furthest from the delivery tube, however, will result in a more easily folded fluid bladder.

As precisely described the bladder assembly is inserted into the housing before inflation. After inflation, internal pressure will drive the fluid bladder to expand along its length, unfolding as it does so. Because the bladder is constrained between the cap and the matrix, however, this unfolding will occur gradually as the matrix shrinks in size. Thus a fluid bladder folded as in FIG. 5 would tend to expand through a partially unfolded configuration as shown in FIG. 6, potentially ending in a fully extended unfolded configuration as shown in FIG. 7.

When the bladder assembly 40 is used in place of bladder assembly 30 in an intraruminal device 10 as shown in FIG. 2, the tendency of the fluid bladder to unfold will drive the medicament 20 toward the first end of the intraruminal device as discussed in connection with the first embodiment. Bladder assembly 40 may also be located in space 46 of an intraruminal device 44 lacking retention wings as shown in FIG. 10.

Referring now to FIGS. 8 and 9, a bladder assembly 50 for use in a third embodiment of an intraruminal device is shown. The bladder assembly 50 has a leading fluid bladder 31 and at least one fluid bladder 32. The fluid bladders communicate with each other through bladder passageways 34. Bladder assembly 50 has a fluid delivery tube 38 and a check valve 39 (not shown). FIG. 8 shows the bladder assembly in a compressed configuration, while FIG. 9 shows the bladder assembly in an expanded configuration. In this embodiment the fluid bladders are essentially centrally located along an axis passing through the plurality of bladders, allowing expansion or contraction like an accordion.

When bladder assembly 50 is put in intraruminal device 10 or 44 and inflated, each individual fluid bladder 31,32 will tend to inflate, driving the bladder assembly 50 away from the collapsed configuration shown in FIG. 8 toward the expanded configuration shown in FIG. 9. As the bladder assembly tends toward the expanded configuration it will elongate and thus drive the medicament 20 toward the first end of the intraruminal device as discussed in connection with the first embodiment.

While the individual fluid bladders in bladder assembly 50 are depicted in FIGS. 8 and 9 as being circular when viewed from above, the fluid bladders may take any other suitable shape that will fit in the intraruminal device and allow communication between the fluid bladders.

In a fourth embodiment of the invention, no bladder assembly is used. A plunger or piston 28 is placed in the housing. The plunger or piston can slide along the length of the housing and creates a fluid-tight seal against the inner surface of the housing. A means for retaining fluid pressure is built into the device, either by molding or by insertion. The fluid pressure retention means may be located in the cap 14. After loading the device with medicament and prior to insertion of the intraruminal device, the region between the second end and the piston is pressurized with fluid to an initial pressure of at least 1, preferably 10, preferably 20, preferably 30, preferably 35, preferably 50 psig. The fluid pressure drives the piston against the medicament, forcing the medicament toward the first end of the device.

The medicament within the matrix to be dispensed by the invented device can be any known medicament suitable for time release dispensation that can be dispersed in a matrix. Suitable medicaments include, but are not limited to, vitamins, antibiotics, growth promotants, hormones, antimicrobials, minerals, amino acids, proteins, and maintenance dose medications.

The size of an intraruminal device 10 according to the invention will vary depending upon the particular ruminant with which it is used.

Although the hereinabove described embodiments of the invention constitute the preferred embodiments, it should be understood that modifications can be made thereto without departing from the scope of the invention as set forth in the appended claims.

What is claimed is:

1. An intraruminal device for the time release dispensation of a medicament, said device comprising:
    a housing;
    a bladder assembly disposed within said housing, said bladder assembly comprising a fluid bladder folded inwardly on itself at least one time; and
    a piston slidably mounted within said housing for applying a compressive force against the medicament when said fluid bladder is inflated with a compressible fluid.

2. An intraruminal device for the time release dispensation of a medicament, said device comprising a housing and a bladder assembly disposed within said housing, said bladder assembly comprising a leading fluid bladder and one or more fluid bladders, said leading fluid bladder and one or more fluid bladders being connected in series via bladder passageways, wherein the bladder passageways are arranged near the edge of said fluid bladders and said fluid bladders are folded alternately one over the other in a zig-zag arrangement.

3. The intraruminal device of claim 2, said bladder assembly further comprising a fluid delivery tube attached to said leading fluid bladder for the delivery of a pressurizing fluid therein, said fluid delivery tube having a means for retaining fluid pressure therein.

4. The intraruminal device of claim 3, said pressurizing fluid being a pressurizing gas, said bladder assembly being initially pressurized with said gas to a pressure of at least 1 psig.

5. The intraruminal device of claim 3, wherein said housing and bladder assembly are all made from a plastic material.

6. An intraruminal device for the time release dispensation of a medicament, said device comprising a housing and a bladder assembly disposed within said housing, said bladder assembly comprising a leading fluid bladder and one or more fluid bladders, said leading fluid bladder and one or more fluid bladders being connected in series via bladder passageways, wherein said bladder passageways are arranged to line up centrally along the axis of the series of fluid bladders in an accordion arrangement.

7. The intraruminal device of claim 6, wherein said device is nonmetallic.

8. The intraruminal device of claim 6, said bladder assembly being made from a flexible elastomeric material.

9. An intraruminal device for the time release dispensation of a medicament, said device comprising:
   a housing;
   a bladder assembly disposed within said housing, said bladder assembly comprising a fluid bladder folded inwardly on itself at least one time, the fluid bladder being initially pressurized with a gas to a pressure of at least 1 psig; and
   an outer surface of said fluid bladder for applying a compressive force against a medicament when said fluid bladder is inflated with said gas.

10. A device according to claim 9, in which the fluid bladder is folded inwardly on itself at least twice.

11. A device according to claim 9, said bladder assembly further comprising a fluid delivery tube attached to said fluid bladder for the delivery of said gas therein, said fluid delivery tube having a check valve therein.

12. A device as in claim 11, wherein said housing, and bladder assembly are all made from a plastic material.

13. A device as in claim 9, wherein said housing and bladder assembly are all made from a plastic material.

14. A device as in claim 9, wherein said device is nonmetallic.

15. A device according to claim 9, further comprising a medicament matrix disposed within said housing between said bladder assembly and a delivery opening in said housing.

16. A method of administering a time release medicament to a ruminant animal comprising the steps of:
   (a) providing an intraruminal device comprising a housing having a first end, a bladder assembly disposed within said housing, and a medicament matrix having said medicament dispersed therein disposed within said housing at said first end thereof, wherein said bladder assembly comprises a plurality of fluid bladders connected in series via bladder passageways;
   (b) pressurizing said bladder assembly to an initial pressure of at least 1 psig to force said medicament matrix against said first end; and
   (c) delivering said device into the rumen of said ruminant animal after said pressurizing step.

17. A method of administering a time release medicament to a ruminant animal comprising the steps of:
   (a) providing an intraruminal device comprising a housing having a first end, a bladder assembly disposed within said housing, and a medicament matrix having said medicament dispersed therein disposed within said housing at said first end thereof, wherein said bladder assembly comprises a fluid bladder folded inwardly on itself at least one time;
   (b) pressurizing said bladder assembly to an initial pressure of at least 1 psig to force said medicament matrix against said first end; and
   (c) delivering said device into the rumen of said ruminant animal after said pressurizing step.

* * * * *